United States Patent
Lin

(10) Patent No.: US 11,596,604 B2
(45) Date of Patent: Mar. 7, 2023

(54) HYDROGEN GENERATOR COOPERATING WITH CLOUD MONITORING SYSTEM AND CLOUD MONITORING SYSTEM THEREOF

(71) Applicant: Hsin-Yung Lin, Shanhai (CN)

(72) Inventor: Hsin-Yung Lin, Shanhai (CN)

( * ) Notice: Subject to any disclaimer, the term of this patent is extended or adjusted under 35 U.S.C. 154(b) by 808 days.

(21) Appl. No.: 16/519,462

(22) Filed: Jul. 23, 2019

(65) Prior Publication Data

US 2020/0030235 A1    Jan. 30, 2020

(30) Foreign Application Priority Data

Jul. 26, 2018  (CN) .......................... 201810830469.6

(51) Int. Cl.
*A61K 9/00* (2006.01)
*A61B 5/00* (2006.01)
(Continued)

(52) U.S. Cl.
CPC .......... *A61K 9/0078* (2013.01); *A61B 5/0803* (2013.01); *A61B 5/7275* (2013.01); *G07C 3/02* (2013.01); *H04L 67/12* (2013.01)

(58) Field of Classification Search
CPC ...... A61B 5/0803; A61B 5/7275; G07C 3/02; H04L 67/12; A61K 9/0078; G08C 2201/42
See application file for complete search history.

(56) References Cited

U.S. PATENT DOCUMENTS

2009/0006218 A1* 1/2009 Ku .......................... G06Q 30/00
                                                        705/26.7
2009/0206023 A1* 8/2009 Rohde ..................... A61M 1/16
                                                        210/321.71
(Continued)

FOREIGN PATENT DOCUMENTS

CA     2964996 A1    4/2016
CA     3014948 A1    2/2019
(Continued)

OTHER PUBLICATIONS

Search Report dated Jan. 9, 2020 for corresponding EP application 19186678.9.
(Continued)

*Primary Examiner* — Nabil H Syed
*Assistant Examiner* — Cal J Eustaquio
(74) *Attorney, Agent, or Firm* — Rosenberg, Klein & Lee

(57) ABSTRACT

A hydrogen generator electrically coupled to a cloud monitoring system comprises a hydrogen generating device, a monitoring device, a network device, and a controlling device. The monitoring device monitors the machine condition of the hydrogen generating device and generates a condition signal. The network device selectively transmits a machine information including the condition signal to the cloud monitoring system. The controlling device receives an operating parameter from the cloud monitoring system via the network device and controls the hydrogen generating device according to the operating parameter. The hydrogen generator monitoring system of the present invention collects the relevant data of the user using the hydrogen generator and tracks the health status of the user to perform big data analysis.

14 Claims, 9 Drawing Sheets

(51) Int. Cl.
  *G07C 3/02* (2006.01)
  *H04L 67/12* (2022.01)
  *A61B 5/08* (2006.01)

(56) References Cited

U.S. PATENT DOCUMENTS

| | | |
|---|---|---|
| 2013/0291128 A1 | 10/2013 | Ito et al. |
| 2015/0100153 A1 | 4/2015 | Lin |
| 2016/0348265 A1 | 12/2016 | Mayer et al. |
| 2017/0044677 A1 | 2/2017 | Kurokawa et al. |
| 2017/0238129 A1 | 8/2017 | Maier et al. |
| 2018/0052964 A1 | 2/2018 | Adelson |
| 2018/0151053 A1 | 5/2018 | Edwards et al. |
| 2018/0158038 A1 | 6/2018 | Lin |
| 2018/0284758 A1* | 10/2018 | Celia .................... G06N 7/005 |

FOREIGN PATENT DOCUMENTS

| | | |
|---|---|---|
| CN | 105311721 A | 2/2016 |
| CN | 107376074 A | 11/2017 |
| CN | 108182763 A | 6/2018 |
| CN | 108320215 A | 7/2018 |
| JP | 2002-291890 A | 10/2002 |
| JP | 2005-523568 A | 8/2005 |
| JP | 2007-531592 A | 11/2007 |
| JP | 2016-099866 A | 5/2016 |
| JP | 2017519547 A | 7/2017 |
| KR | 10-1798818 B1 | 11/2017 |
| RU | 153346 U1 | 7/2015 |
| RU | 2581358 C2 | 4/2016 |
| WO | 2010078558 A1 | 7/2010 |
| WO | WO-2014145218 A2 * | 9/2014 ................ A61J 1/03 |
| WO | 2017136489 A1 | 8/2017 |
| WO | 2018116366 A1 | 6/2018 |

OTHER PUBLICATIONS

Written Opinion dated Feb. 20, 2020 for corresponding SG application 10201906675Y.
Office Action dated Aug. 27, 2020 for corresponding CA application 3,050,568.
Office Action dated Sep. 11, 2020 for corresponding RU application 2019123465.
Notification of Reason For Refusal 2019-132595 dated Oct. 6, 2020 for corresponding JA application.
XP55653933A, "Nebulizer", Wikipedia.
XP55654229A, "De-identification", Wikipedia.
KIPO Notice of Preliminary Rejection dated May 13, 2021 for corresponding KR Application No. 10-2019-0091249.
JPO Notification of Reason of Refusal dated Jun. 8, 2021 for corresponding JP Application No. 2019-132595.
Foreign Official Action Issued by Foreign Patent Office for Corresponding Application No. 2021118128.
Foreign Official Action Issued by Foreign Patent Office for Corresponding Application No. 201810830469.6.
International Official Action Issued By Foreign Patent Office in Appliction No. 19186678.9-1126 dated Aug. 17, 2022.
International Official Action Issued By Foreign Patent Office in Application No. 201810830469.6/2022052402891460 dated May 27, 2022.

* cited by examiner

HYDROGEN GENERATOR COOPERATING WITH CLOUD MONITORING SYSTEM AND CLOUD MONITORING SYSTEM THEREOF

The present application is based on, and claims priority from, China application number 201810830469.6, filed on 2018 Jul. 26, the disclosure of which is hereby incorporated by reference herein in its entirety.

BACKGROUND OF THE INVENTION

Field of the Invention

The present invention relates to a hydrogen generator and a cloud monitoring system, and more particularly to a hydrogen generator capable combined with a cloud service and a cloud monitoring system capable monitoring a plurality of hydrogen generators.

Description of the Prior Art

For long time, people have paid much attention on human life. Many medical technologies have been developed to fight disease and extend human life, but most medical treatments in the past are passive. That is to say, the disease is treated when it occurs, such as surgery, drug administration, chemotherapy and radiotherapy of the cancer, or nursery, rehabilitation, and correction of the chronic disease. However, in recent years, many medical experts have gradually made researches toward preventive medical methods, such as health food research, genetic disease screening, and early prevention, for actively preventing future morbidity. In addition, in order to extend human life, many anti-aging and anti-oxidation technologies have been developed and widely used by the public, including smear-care products and antioxidant foods/drugs.

Studies have found that the unstable oxygen (O+), also known as free radicals (harmful free radicals), produced by the human body for various reasons (such as disease, diet, environment or lifestyle) can be mixed with the inhaled hydrogen to form part of water and then get excreted so that the number of free radicals in the human body can be reduced to regain a healthy alkaline body from an acidic body, to resist oxidation and aging, to eliminate chronic disease, and to achieve beauty care effects. Clinical trials have shown that some long-term bedridden patients who have lung damage caused by long-term breathing high concentrations of oxygen can be relieved by inhaling hydrogen.

Based on the above reasons, in recent years, research on hydrogen has been endless, and related products that generate hydrogen have been developing and manufacturing largely. However, the reaction of the individual who inhales hydrogen may be varied depending on each person's physical condition, but most of the products are limited to manufacturing and sales. There is no corresponding after-sales service and tracking for the customer's response and physiological changes after use, which is an obvious drawback of overall health protection.

SUMMARY OF THE INVENTION

In response to the above-mentioned problems, an objective of the present invention is to provide a hydrogen generator cooperating with a cloud monitoring system. The hydrogen generator comprises a hydrogen generating device, a monitoring device, a network device and a controlling device. The monitoring device is coupled to the hydrogen generating device, the network device is electrically coupled to monitoring device and the controlling device electrically is coupled to the network device. The hydrogen generator is configured to generate hydrogen for a user to inhale, and the hydrogen generator comprises a water tank, an electrolysis cell and a nebulizer. The water tank is configured to accommodate a water to be electrolyzed. The electrolysis cell is configured to electrolyze the water to be electrolyzed to generate a hydrogen gas. The nebulizer is configured to generate an atomized gas and mix with the hydrogen gas to generate a mixed gas for a user to inhale. The monitoring device can be configured to detect or display a condition signal of the hydrogen generating device, and the network device can selectively transmit a machine information including the condition signal to the cloud monitoring system. The controlling device can be configured to receive an operating parameter from the cloud monitoring system via the network device and control the hydrogen generating device according to the operating parameter.

Wherein the condition signal can comprise a hydrogen production information, a usage time information, a hydrogen concentration information, a nebulizer atomization rate information, or a hydrogen generator temperature information.

Other objective of the present invention is to provide a cloud monitoring system for monitoring a plurality of hydrogen generators as said. The cloud monitoring system comprises a cloud control console, an integrated database, a remote transmission device, a position monitoring device and a data analysis device. The remote transmission device is coupled to the cloud control console, the position monitoring device is coupled to the integrated database, and the data analysis device is coupled to the integrated database. The cloud control console can be configured to receive a plurality of machine information from the plurality of hydrogen generators, and the integrated database is configured to store the plurality of machine information. The remote transmission device can be configured to transmit an operating parameter to a first hydrogen generator of the plurality of hydrogen generators, whereby the first hydrogen generator can perform a power-on procedure, a turn-off procedure or a setting procedure according to the operating parameter. The position monitoring device can be configured to display or record the position of the plurality of hydrogen generators, and the data analysis device can be configured to analyze and ascertain the plurality of machine information.

Other objective of the present invention is to provide a cloud monitoring system for monitoring a plurality of hydrogen generators as said. The cloud monitoring system comprises an integrated database, an ordering platform, a cloud control console, a remote transmission device and a position monitoring device. The ordering platform is coupled to the integrated database via network, the remote transmission device is coupled to the cloud control console, and the position monitoring device coupled to the integrated database. The integrated database is configured to store the plurality of machine information of the plurality of hydrogen generators, the cloud control console is configured to generate a plurality of activation parameters respectively corresponding to the plurality of machine information, and the plurality of hydrogen generators can respectively perform an activation setting procedure according to the activation parameter. The ordering platform is configured for a user to input an order instruction and transmits the order instruction to the cloud control console, wherein the order instruction comprises a predetermined position information. The position monitoring device can be configured to display the position of the plurality of hydrogen generators.

In this embodiment, when the cloud control console compares the position with the predetermined position information of a first hydrogen generator of the plurality of hydrogen generators, the result is matched. Then, the cloud control console controls the remote transmission device to output the activation parameter corresponding to the first hydrogen generator. Thereby, the first hydrogen generator can perform the activation setting procedure according to the activation parameter.

Compared with the prior art, the cloud monitoring system of the hydrogen generator of the present invention uses the monitoring device of the hydrogen generator to collect the machine information of the hydrogen generator and uses the physiological information input device to track the physiological information of the user. The cloud monitoring system of the hydrogen generator of the present invention uses the machine information and physiological information for big data analysis, and applies the analysis results to product improvement, after-sales service and even medical research.

BRIEF DESCRIPTION OF THE APPENDED DRAWINGS

Some of the embodiments will be described in detail, with reference to the following figures, wherein like designations denote like members, wherein.

The advantages, spirits, and features of the present invention will be explained and discussed with embodiments and figures as follows.

DETAILED DESCRIPTION OF THE INVENTION

In order to make the advantages of the present invent, the spirit and features can be more easily and clearly understood, the detailed description and discussion will be followed by specific embodiments and with reference to the accompanying figures. It is noted that the specific embodiments are merely representative of the specific embodiments of the present invention, and the specific methods, devices, conditions, materials, and the like are not intended to limit the invention or the corresponding embodiments. Moreover, the devices in the figures are only used to express their relative positions and are not drawn in their actual proportions.

Figure 1:
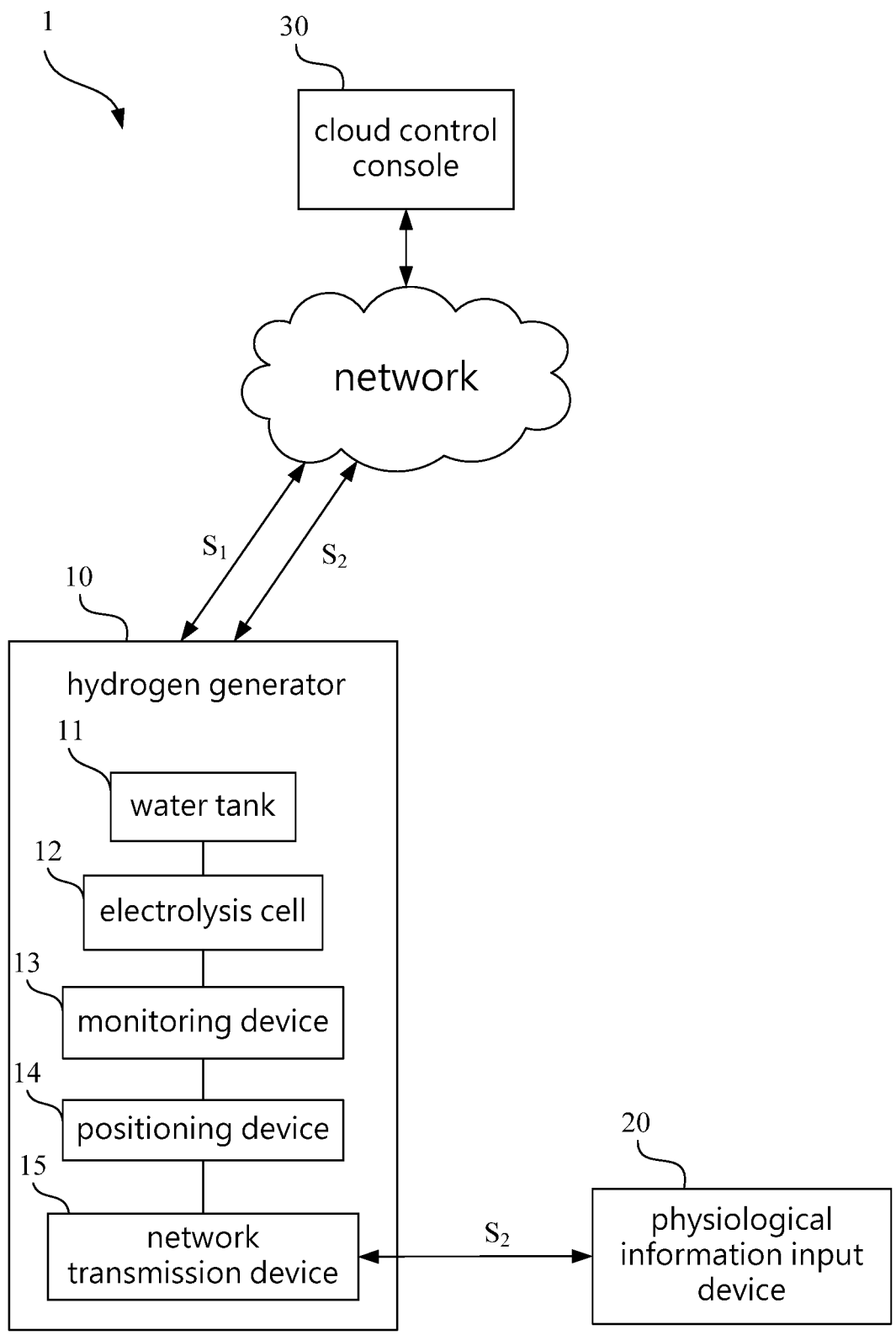
FIG. 1 is a function block diagram illustrating the cloud monitoring system of the hydrogen generator according to an embodiment of the present invention.

Please refer to FIG. 1. FIG. 1 is a function block diagram illustrating the cloud monitoring system of the hydrogen generator 1 according to an embodiment of the present invention. The present invention provides a cloud monitoring system of a hydrogen generator 1, comprising a hydrogen generator 10, a physiological information input device 20 and a cloud control console 30. The hydrogen generator 10 is configured to generate hydrogen for a user to inhale, and the hydrogen generator 10 comprises a water tank 11, an electrolysis cell 12, a monitoring device 13, a positioning device 14 and a network transmission device 15. The water tank 11 is configured to accommodate a water to be electrolyzed. The electrolysis cell 12 is configured to electrolyze the water to be electrolyzed to generate a hydrogen gas. The monitoring device 13 is configured to detect a condition signal. The positioning device 14 is configured to generate a positioning signal of the hydrogen generator. The network transmission device 15 is electrically coupled to the monitoring device 13 and the positioning device 14 is configured to transmit a machine information $S_1$ including the condition signal and the positioning signal to the cloud control console 30. The physiological information input device 20 is configured to receive the machine information $S_1$ and the physiological information $S_2$, and performs data analysis, using the machine information $S_1$ and the physiological information $S_2$.

Wherein the condition signal includes a hydrogen production information, a usage time information, a hydrogen concentration information, a hydrogen generator gas pressure information, or a hydrogen generator temperature information, etc., which may be sensed by a plurality of sensors built in the hydrogen generator. The hydrogen production information could be the average hydrogen production per minute, the total hydrogen production or the maximum hydrogen production, etc. The usage time information could be the average daily usage time, the usage period or the total usage time. The hydrogen concentration information could be measured by a hydrogen concentration sensor built in the hydrogen generator. The hydrogen generator gas pressure information could be measured by a pressure sensor built in the hydrogen generator. The hydrogen generator temperature information may be, but is not limited to, the motor temperature information of the hydrogen generator, the electrolysis water temperature information, or the hydrogen temperature information.

The physiological information $S_2$ could comprise various physiological related information such as height value, body weight value, age, gender, blood oxygen concentration value, blood glucose concentration value, respiratory function value, blood pressure value and X-ray film. In a specific embodiment, the physiological information input device 20 could manually input the physiological information $S_2$ by the user, and communicate with the hydrogen generator 10 in a wired or wireless manner. The physiological information $S_2$ is transmitted to the cloud control console 30 by the network transmission device 15 of the hydrogen generator 10. In other embodiment, the physiological information input device 20 could be a physiological information sensor, and the physiological information sensor communicates with the hydrogen generator 10 in a wired or wireless manner. The physiological information $S_2$ is transmitted to the cloud control console 30 by the network transmission device 15. The physiological information sensor is electrically coupled to the hydrogen generator 10 in a wired manner, such as an oxygen mask, or a heart rate meter. The physiological information sensor is electrically coupled to the hydrogen generator 10 in a wireless manner, such as a home detecting instrument (for example, a blood pressure machine or a weight machine) having a wireless transmission function, or a wearable device (for example, a smart wristband), but is not limited thereto. In other embodiment, the physiological information sensor has a transmission device for uploading the physiological information $S_2$ to the cloud control console 30 by itself, for example, a medical level professional detecting instrument (for example, a nuclear magnetic resonance instrument, an ultrasonic detector), which is convenient for the user. When the instrument is used in the hospital, the physiological information $S_2$ could be directly uploaded to the cloud control console 30.

Figure 2:
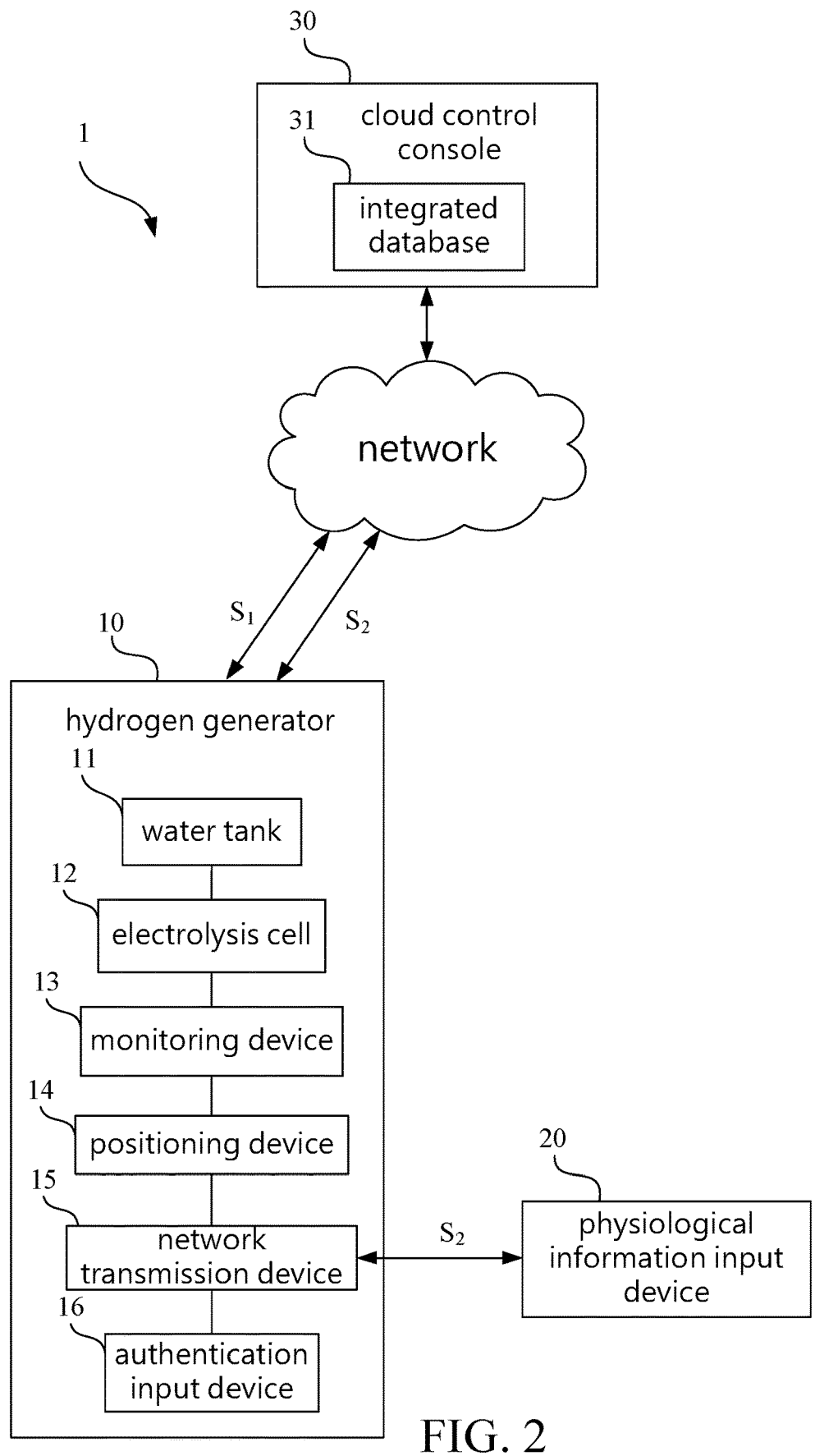
FIG. 2 is a function block diagram illustrating the cloud monitoring system of the hydrogen generator according to an embodiment of the present invention.

Please refer to FIG. 2. FIG. 2 is a function block diagram illustrating the cloud monitoring system of the hydrogen generator 1 according to an embodiment of the present invention. In one embodiment, the hydrogen generator 10 comprises an authentication input device 16, and the cloud control console 30 comprises an integrated database 31. The user is electrically coupled to the cloud control console 30 through the network, and establishes a user account in the integrated database 31. The user account comprises basic information (e.g. age, gender, and medical history), the identifier of the hydrogen generator by the user, and at least one authentication information. Wherein the authentication information may be a password, a fingerprint authentication, a pupil authentication, a voice authentication, a USB authentication, a mobile phone authentication, an application authentication, a device identification code authentication, etc., but are not limited thereto. When the user uses the hydrogen generator 10, the user inputs a first authentication information via the authentication input device 16. The first authentication information is included in the machine information $S_1$ and transmitted to the cloud control console 30. The cloud control console 30 compares the first authentication information of the machine information $S_1$ with the authentication information included in the user account. If the first authentication information matches at least one of the authentication information of the user account, the machine information $S_1$ is stored in the user account of the integrated database 31. Similarly, when the user uses the physiological information input device 20, the physiological information $S_2$ is transmitted to the hydrogen generator 10. The user could input a second authentication information via the authentication input device 16 of the hydrogen generator 10. The second authentication information is included in the physiological information $S_2$ and transmitted to the cloud control console 30. The cloud control console 30 compares the second authentication information of the physiological information $S_2$ with the authentication information included in the user account. If the second authentication information matches at least one of the authentication information of the user account, the physiological information $S_2$ is stored in the user account of the integrated database 31. In other embodiment, the user could input the second authentication information via the physiological information input device 20. The second authentication information is included in the physiological information $S_2$ and transmitted to the hydrogen generator 10, and the physiological information $S_2$ is transmitted to the cloud control console 30 via the network transmission device 15 of the hydrogen generator 10. Wherein the second authentication information is the user's physiological characteristic information, setting password, fingerprint information authentication, pupil information authentication, voice information authentication, USB information authentication, mobile phone authentication, application authentication, device identification code authentication, etc., but is not limited thereto. The first authentication information may be the same authentication information as the second authentication information.

In one specific embodiment, when there is only single user for the hydrogen generator 10 and the physiological information input device 20, a machine identification code and a device identification code electrically coupled to the user account could be set by the could control console 30 without an authentication step. For example, the user A establishes a user account B, and connects the device identification code of a smart bracelet with the user account B. When the cloud control console 30 receives the physiological information $S_2$ that comprises the device identification code of a smart bracelet, the physiological information $S_2$ is automatically stored in the user account B. Wherein the device identification code could be a unique serial number.

Figure 3:
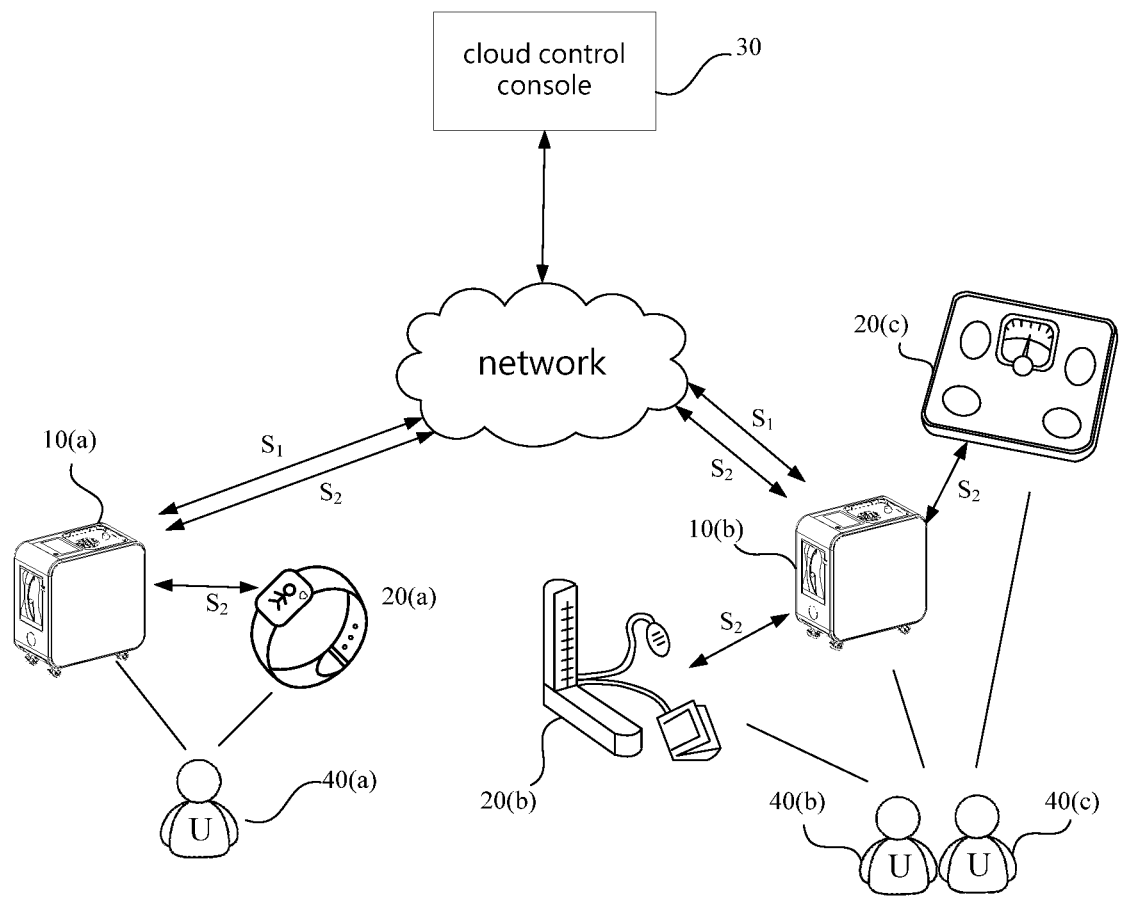
FIG. 3 is a schematic diagram illustrating the cloud monitoring system of the hydrogen generator according to an embodiment of the present invention.

Please refer to FIG. 3. FIG. 3 is a schematic diagram illustrating the cloud monitoring system of the hydrogen generator 1 according to an embodiment of the present invention. In one embodiment, the cloud monitoring system of the hydrogen generator 1 of the present invention is applied to a plurality of users including user 40(a), user 40(b), user 40(c), hydrogen generator 10(a), hydrogen generator 10(b), physiological information input device 20(a), physiological information input device 20(b) and physiological information input device 20(c). In this embodiment, each user has at least one authentication information and each hydrogen generator has a machine identification code. By using the authentication information of each user cooperate with the machine identification code, it is possible to realize an identification function of the plurality of users using the plurality of hydrogen generators and the plurality of physiological information input devices.

Figure 4:
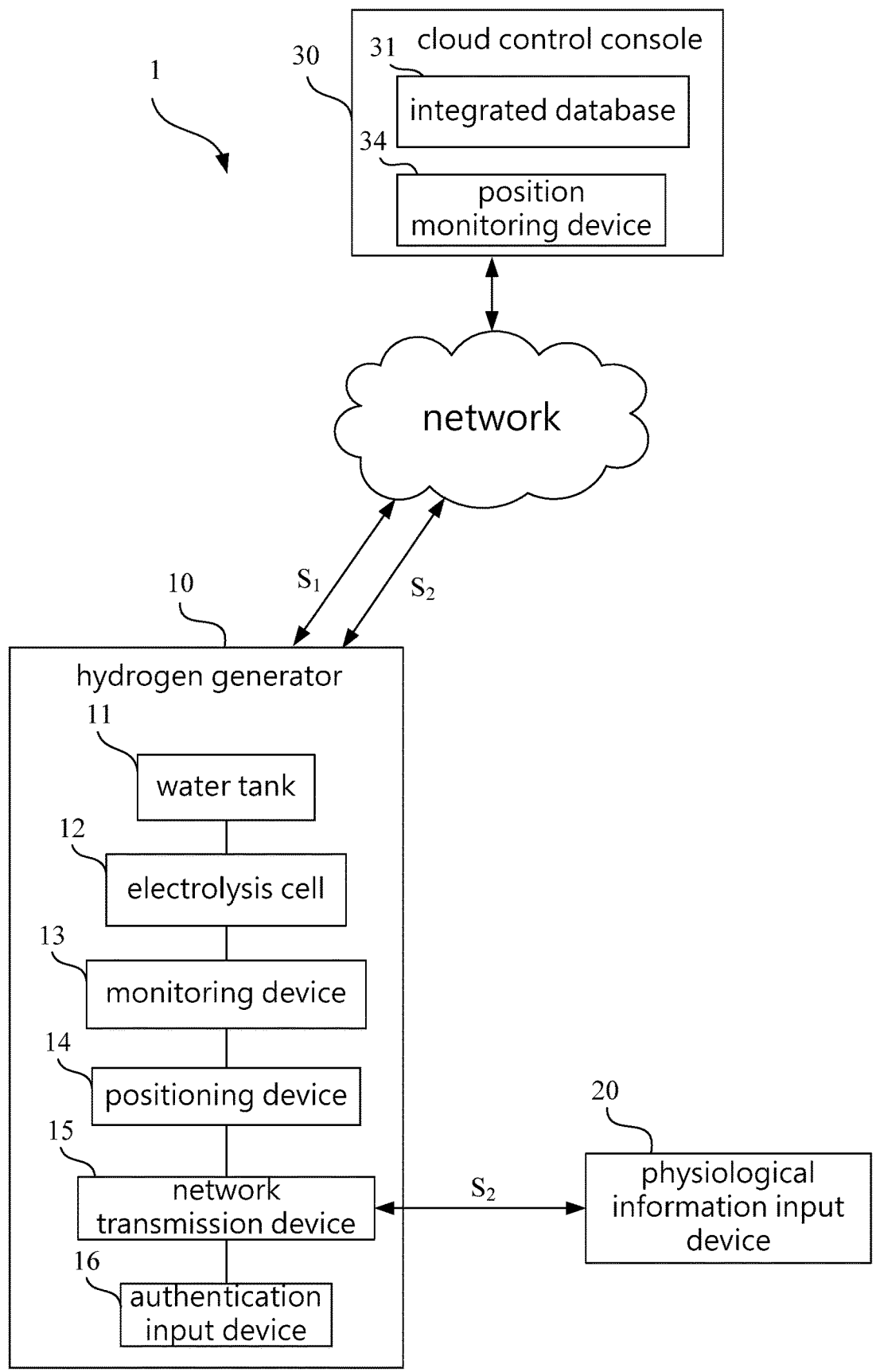
FIG. 4 is a function block diagram illustrating the cloud monitoring system of the hydrogen generator according to an embodiment of the present invention.
Figure 5:
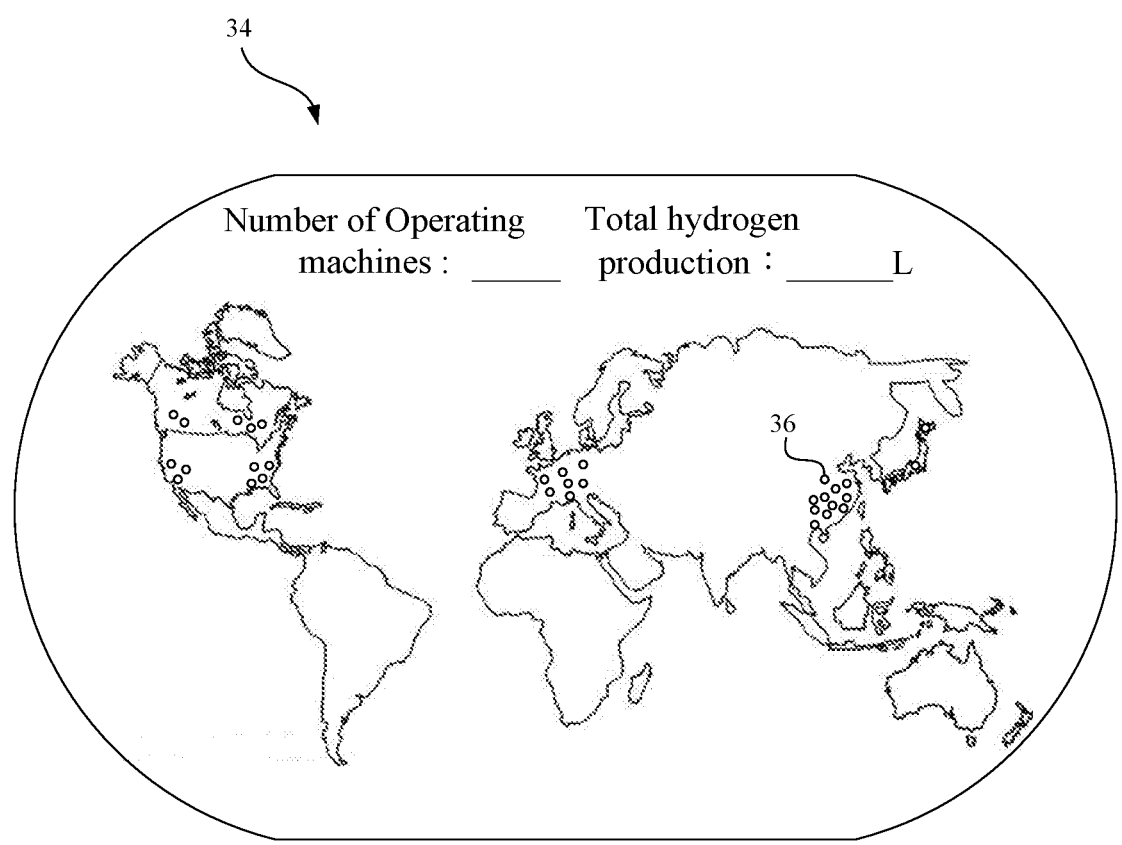
FIG. 5 is a schematic diagram illustrating the position monitoring device of the cloud monitoring system of the hydrogen generator according to an embodiment of the present invention.

Please refer to FIG. 4 and FIG. 5. FIG. 4 is a function block diagram illustrating the cloud monitoring system of the hydrogen generator 1 according to an embodiment of the present invention. FIG. 5 is a schematic diagram illustrating the position monitoring device 34 of the cloud monitoring system of the hydrogen generator 1 according to an embodiment of the present invention. In one specific embodiment, the cloud monitoring system 1 comprises a position monitoring device 34, and the positioning device 14 could be a GPS (Global Position System) positioning device or a positioning device that generates a machine network address information. The position monitoring device 34 is configured to detect a positioning signal 36 of the hydrogen generator 10, and transmits the positioning signal 36 including the machine information $S_1$ to the cloud control console 30. As shown in FIG. 5, the position monitoring device 34 could be a digital world map, and the digital world map could display various information, such as total hydrogen production and the number of operating machines. When the cloud control console 30 receives the machine information $S_1$, the positioning signal 36 of the machine information $S_1$ is marked in the corresponding position of the position monitoring device 34. In the position monitoring device 34, the marked points of each of positioning signals 36 represent an operating hydrogen generator 10. In practical applications, the positioning signal 36 indicated in the position monitoring device 34 could be set one marked point which represents not only one hydrogen generator 10, but also more hydrogen generators 10 via the cloud control console 30. In practical applications, the positioning signal 36 indicated in the position monitoring device 34 could also convey different signals through the marked point. For example, when the marked point flickering may represent a machine failure, the color change of the marked point may indicate that the hydrogen production amount is lower than the average value, and various information may be conveyed by the marked point, and is not limited thereto.

In one specific embodiment, the user or the administrator may view a historical information or statistical data of the user account by accessing the cloud control console 30. The user may access the personal user account or the user account authorized to access by inputting the authentication information, and access relevant historical information, such as the average blood pressure value in the past three months, the weight change in one year, the cumulative hydrogen production amount of the hydrogen generator used, and the comparison chart of inhaled hydrogen and blood pressure changes. Administrator can choose to display different types of statistical data by accessing the cloud control console 30, such as depending on the condition of the machine (used or damaged), the area of use, the type of user (different disease, gender, age, etc.), the average amount of hydrogen production, and usage time. In one specific embodiment, the administrator can also access the personal user account authorized to be viewed by the administrator for data analysis purposes, and give the user appropriate feedback. For example, the cloud control console 30 can calculate the user's recommended usage hours and machine setting parameters according to the machine information $S_1$ and the physiological information $S_2$ provided by the user, and the feedback to the user. In other specific embodiment, the administrator can read a de-identified user data for big data analysis through the cloud control console 30, or the user performs de-identification processing before uploading the data to protect the security of user profiles.

Figure 6:
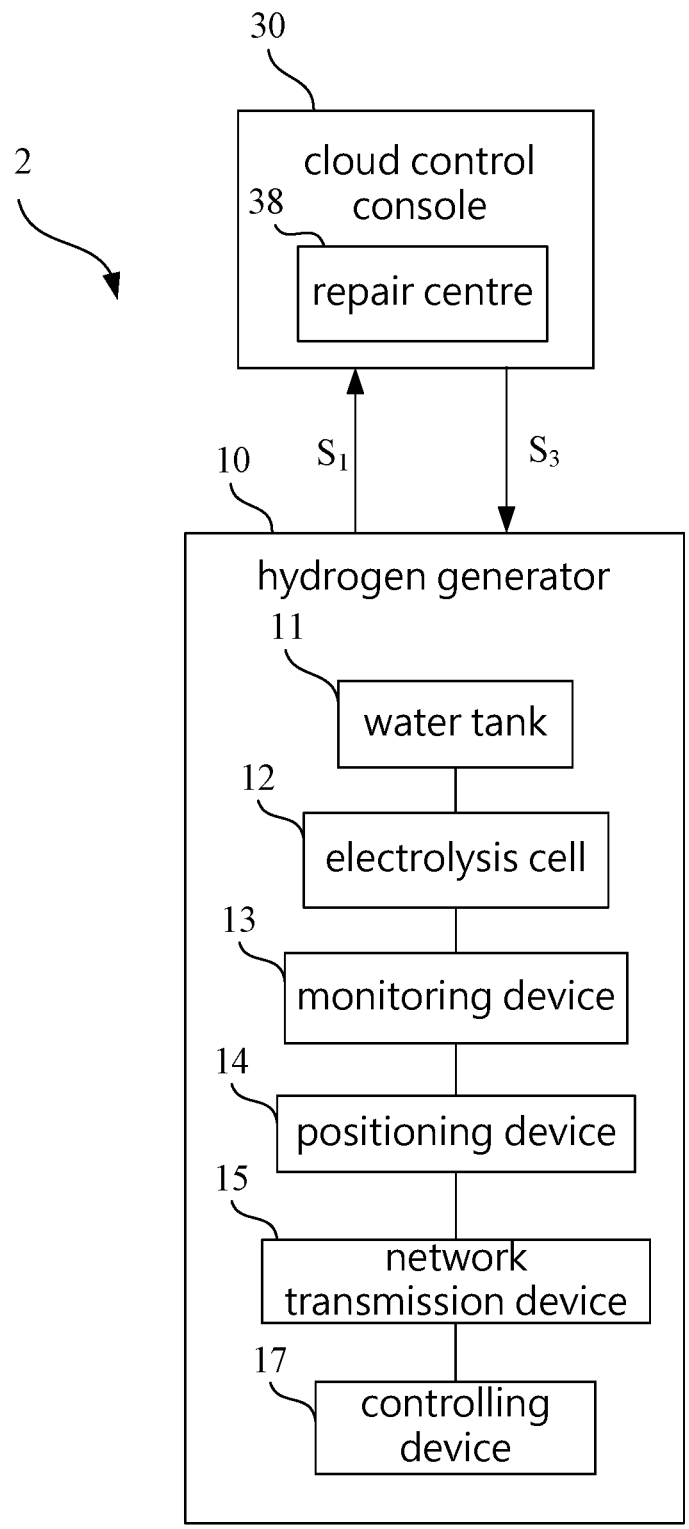
FIG. 6 is a function block diagram illustrating the repair centre of the hydrogen generator according to an embodiment of the present invention.

Please refer to FIG. 6. FIG. 6 is a function block diagram illustrating the repair centre 38 of the hydrogen generator according to an embodiment of the present invention. In one embodiment, a remote control system of hydrogen generator 2 of the present invention comprises a hydrogen generator 10 and the cloud control console 30; the cloud control console 30 includes a repair centre 38. The hydrogen generator 10 is configured to generate hydrogen for a user to inhale, and the hydrogen generator 10 includes a water tank 11, an electrolysis cell 12, the monitoring device 13, a positioning device 14, a network transmission device 15, and a control device 17. The water tank 11 is configured to accommodate a water to be electrolyzed. The electrolysis cell 12 is configured to electrolyze the water to be electrolyzed to generate a hydrogen gas. The monitoring device 13 is configured to detect a condition signal. The positioning device 14 is configured to generate a positioning signal of the hydrogen generator. The network transmission device 15 is configured to transmit a machine information $S_1$ including the condition signal and the positioning signal to the cloud control console 30, and is configured to receive a control information $S_3$ sent from the cloud control console 30. The control device 17 is configured to receive the control information $S_3$, and perform the hydrogen generator 10 according to the control information $S_3$.

In one specific embodiment, the cloud control console 30 receives the machine information S1, and monitors the condition signal. If the condition signal indicates that the machine is abnormal, and the abnormal condition such as an expiration of service life, an abnormal hydrogen production amount, an abnormal temperature of machine, and an abnormal hydrogen concentration, the cloud control console 30 transmits a repair information to the repair centre 38. The repair information comprises the positioning signal of the abnormal hydrogen generator, the user (purchaser) contact information, and the abnormality diagnosis. The repair centre 38 receives the repair information, and ascertains the abnormal condition according to the abnormality diagnosis of the repair information. If it is ascertained that the abnormal condition is a non-hardware facility abnormality, a control information $S_3$ is sent to the network transmission device 15 of the hydrogen generator 10 through the cloud control console 30. The control device 17 is electrically coupled to the network transmission device 15 and receives control information $S_3$ by the network transmission device 15. The control device 17 performs the hydrogen generator 10 to perform abnormal state troubleshooting according to the content of the control information S3. The control device 17 can perform the operation program such as turn-on and turn-off, the flow rate setting, the system option setting, and the system internal code setting of the hydrogen generator 10 according to the control information $S_3$.

In one specific embodiment, the repair centre 38 ascertains the risk level of the abnormal event according to the abnormal diagnosis of the repair information. If the risk level is high, the repair centre 38 performs an initial treatment through remote control. If the risk level is low, the repair centre 38 contacts to the user to explain the abnormal condition of the machine and reserve the repair time. In the above specific embodiment, the user has the right to set whether or not to agree to the remote control to protect the privacy of the user.

In one specific embodiment, the user can transmit the control information $S_3$ to the control device 17 of the hydrogen generator 10 authorized to perform through a mobile device for simple operations, such as turn-on and turn-off.

In one specific embodiment, the cloud monitoring system of the hydrogen generator 1 of the present invention uses the machine information $S_1$ and the physiological information $S_2$ for big data analysis, which is applied to medical research. For example, the study on whether it is helpful to improve symptoms for the patients with Parkinson's disease after inhaling hydrogen. In other embodiment, the cloud monitoring system of the hydrogen generator 1 of the present invention analyzes the machine information $S_1$ and the physiological information $S_2$, and the analysis is then applied for after-sales service. For example, when the cloud monitoring system of the hydrogen generator 1 detects an abnormality of the hydrogen generator 10, the system actively contacts the user for repairment. In other embodiment, the cloud monitoring system of the hydrogen generator 1 of the present invention performs big data analysis with the machine information $S_1$ and the physiological information $S_2$ and applies it for product improvement. For example, data analysis shows that the probability of failure of the hydrogen generator in the southeast coast is high, and the cause of the malfunction is mostly temperature anomaly. Therefore, it is judged that the local climate environment may be hot to increase the probability of malfunction, so that the improvement of machine is executed. In other embodiment, the cloud monitoring system of the hydrogen generator 1 of the present invention performs big data analysis of the machine information $S_1$ and the physiological information $S_2$ and applies it for user's feedback. For example, the user can access the cloud control console 30 to view the user's own machine information $S_1$ and physiological information $S_2$, and examine the trend of the body value after starting to use the hydrogen generator. In other embodiment, the cloud monitoring system of the hydrogen generator 1 of the present invention broadcasts video or advertising messages to the hydrogen generator 10 via the cloud control console 30, and the broadcast message comprises, but not limited to, system upgrade information, new model information, sponsored advertisements content information, etc.

Figure 7:
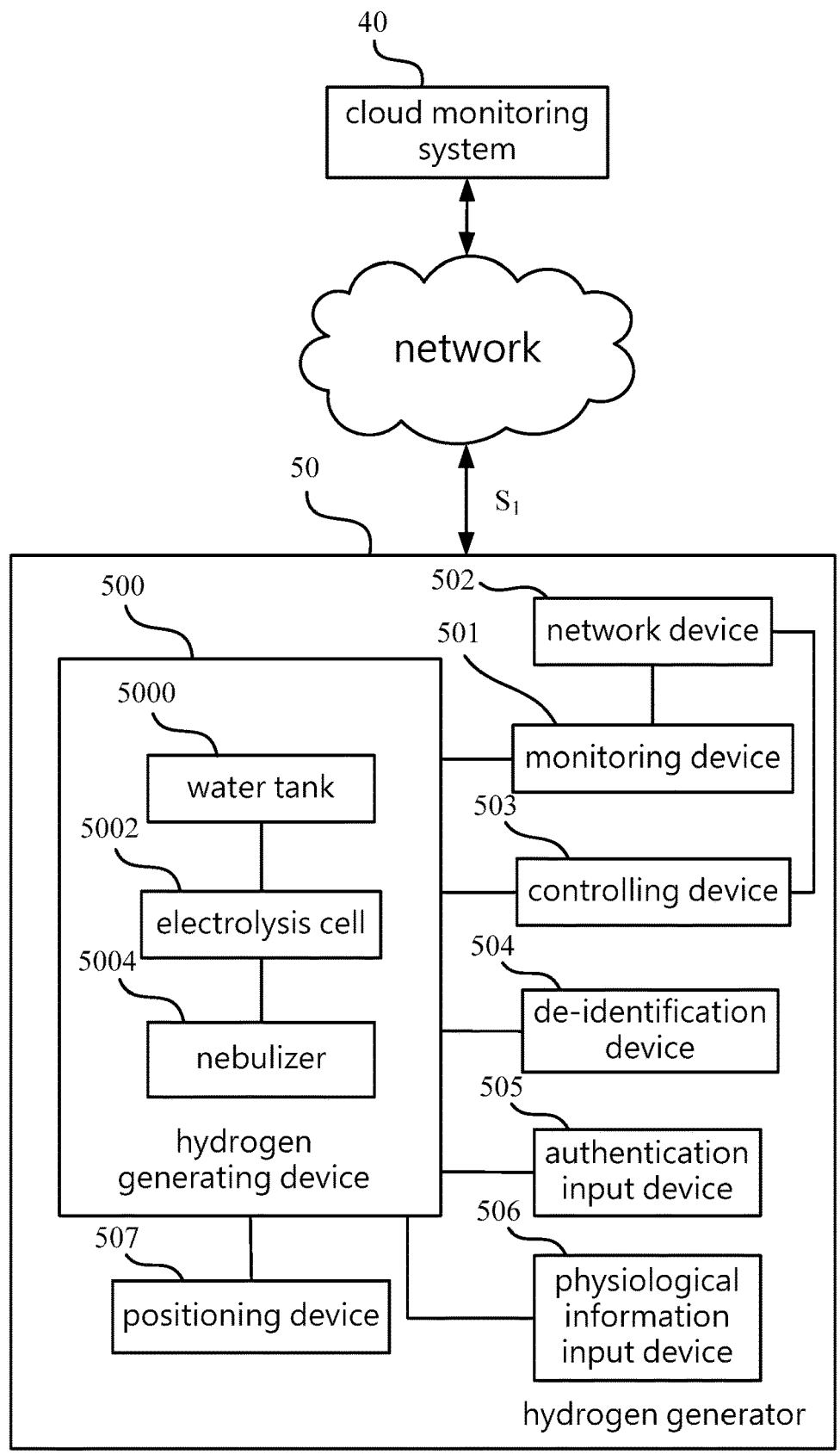
FIGS. 7 and 8 are function block diagrams illustrating the cloud monitoring system and the hydrogen generator according to an embodiment of the present invention.
Figure 8:
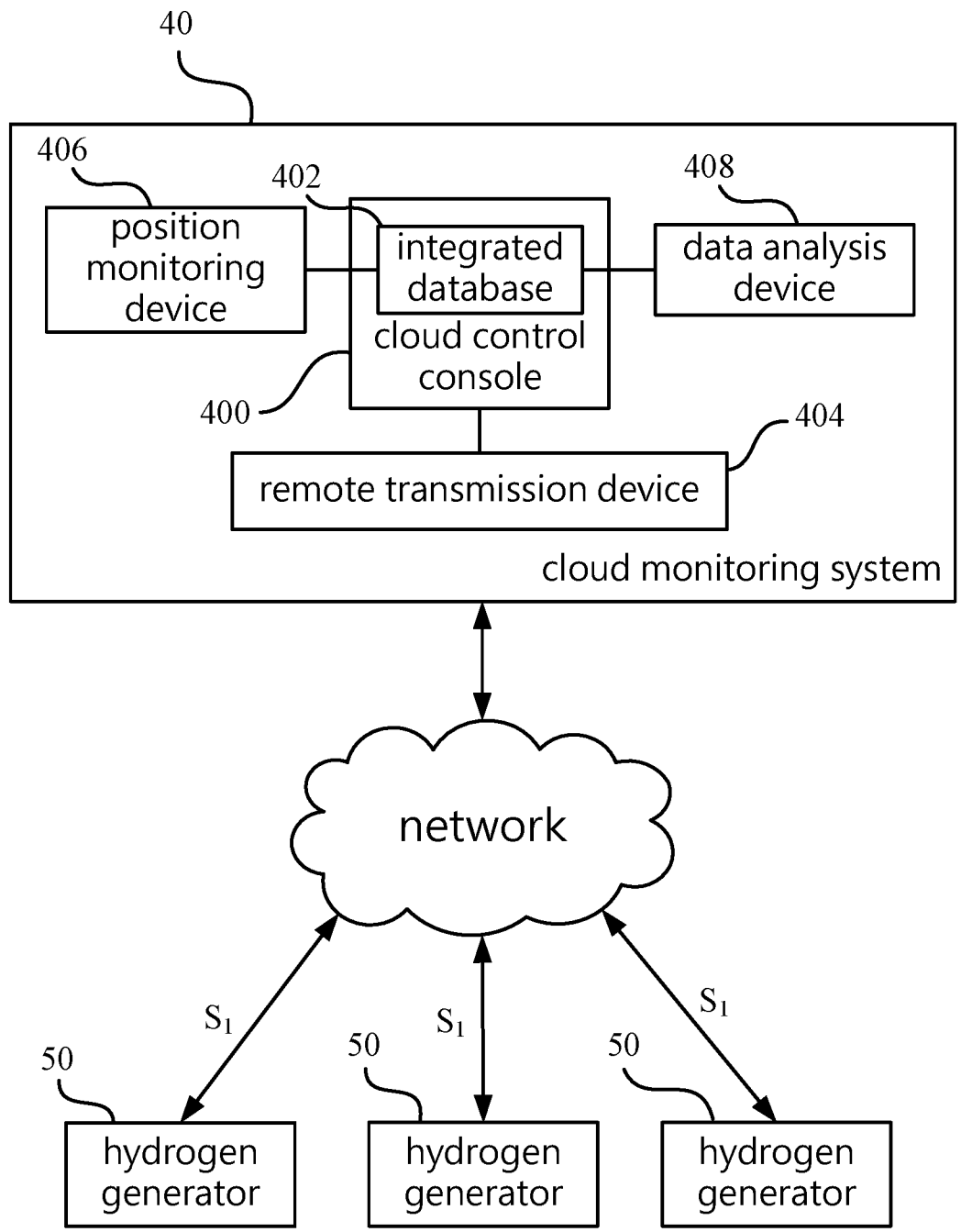

Please both refer to FIG. 7 and FIG. 8. FIGS. 7 and 8 are function block diagrams illustrating the cloud monitoring system 40 and the hydrogen generator 50 according to an embodiment of the present invention. For the sake of simplicity of the drawing, the internal detailed structure of the cloud monitoring system 40 is omitted in FIG. 7, and the internal detailed structure of the hydrogen generator 50 is omitted in FIG. 8. As shown in FIG. 7, the cloud monitoring system 40 and the hydrogen generator 50 are interconnected via a network, so that the hydrogen generator 50 can transmit the machine information $S_1$ to the cloud monitoring system 40. In addition, the cloud monitoring system 40 can simultaneously couple the plurality of hydrogen generators 50 through the network, as shown in FIG. 8. However, for the sake of clarity of the figure, FIG. 7 only illustrates one hydrogen generator 50. The cloud monitoring system 40 receives the machine information $S_1$ respectively transmitted by the respective hydrogen generators 50, then performs big data analysis of the machine information $S_1$, and can transmit corresponding operating parameters to the respective hydrogen generators 50.

In this embodiment, the hydrogen generator 50 comprises the hydrogen generating device 500, the monitoring device 501, a network device 502, and a controlling device 503. Wherein the monitoring device 501 is coupled to the hydrogen generating device 500. The network device 502 is electrically coupled to the monitoring device 501, and is coupled to the network to be coupled to the cloud monitoring system 40. The controlling device 503 is electrically coupled to the network device 502. The hydrogen generating device 500 further comprises the water tank 5000 for accommodating water to be electrolyzed, the electrolysis cell 5002, and a nebulizer 5004. Wherein the electrolysis cell 5002 can be configured to electrolyze water to generate hydrogen gas, and the nebulizer 5004 can generate an atomized gas and mix the atomized gas with the hydrogen gas to generate a mixed gas for the user to inhale.

The monitoring device 501 can be configured to detect the condition of the hydrogen generating device 500, and generate or display the condition signal according to the machine condition. The condition signal can comprise the hydrogen production information, the usage time information, and the hydrogen concentration information, a nebulizer atomization rate information, or the hydrogen generator temperature information. The network device 502 can selectively transmit the machine information $S_1$ including the condition signal to the cloud monitoring system 40. In practice, the network device 502 can be configured to automatically transmit the machine information $S_1$ after a certain time or a certain number of use, or the network device 502 is instructed by the user to transmit. The controlling device 503 can receive an operating parameter from the cloud monitoring system 40 by the network device 502 and control the hydrogen generating device 500 according to the operating parameter. In practice, the operating parameter may be generated and transmitted by the cloud monitoring system 40, or may be sent by the user to the cloud monitoring system 40 through a mobile device and then transmitted to the control device 503 by the cloud monitoring system 40.

As mentioned above, the monitoring device 501 located in the hydrogen generator 50 can upload the machine condition to the cloud monitoring system 40 through the network device 502, so that the cloud monitoring system 40 can save the machine information and perform the big data analysis of the machine information for medical research. On the other hand, the remote hydrogen generator 50 can also be manipulated through the cloud monitoring system 40. For example, when the machine information $S_1$ comprises abnormal information, the operating parameter transmitted by the cloud monitoring system 40 to the controlling device 503 may be a turn-off or setting parameter. After receiving the operating parameters, the controlling device 503 can perform a turn-off procedure or a setting procedure of the hydrogen generating device 500, thereby eliminating obstacles to the abnormality of the machine.

In addition, as shown in FIG. 7, the hydrogen generator 50 of this embodiment further comprises a de-identification device 504, the authentication input device 505, the physiological information input device 506, and the positioning device 507 for performing de-identification, generating user's authentication information, generating user's physiological information, and generating location information, respectively. The functions of the de-identification device 504, the authentication input device 505, the physiological information input device 506, and the positioning device 507 of this embodiment are substantially the same as those of the corresponding devices in the foregoing specific embodiments, and thus will not be described again. It should be noted that although the hydrogen generator 50 in FIG. 7 comprises all of the above devices, the practical application is not limited thereto, and at least one of the above devices may be provided as needed. The de-identification device 504 performs data de-identification in the hydrogen generator 50 instead of being performed by the cloud monitoring system 40, thereby ensuring data privacy. The de-identification device 504 can be ascertained whether to enable or identify the data by the user. For example, the de-identification device 504 can utilize the differential privacy method to the machine information $S_1$ and/or the physiological information $S_2$ generated by the hydrogen generator 50, and then transmit the de-identify machine information $S_1$ and/or the de-identify physiological information $S_2$ to the cloud monitoring system 40.

Please refer to FIG. 8 again. As shown in FIG. 8, the cloud monitoring system 40 comprises the cloud control console 400, the integrated database 402, the remote transmission device 404, the position monitoring device 406, and a data analysis device 408. Wherein the remote transmission device 404 is coupled to the cloud control console 400, the position monitoring device 406 is coupled to the integrated database 402, and the data analysis device 408 is coupled to the integrated database 402. The integrated database 402 can be comprised in the cloud control console 400, or can be coupled to the cloud control console 400, as shown in the foregoing specific embodiments.

In this embodiment, the cloud control console 400 can receive the plurality of machine information $S_1$ of the plurality of hydrogen generators 50 from the network and store them in the integrated database 402. The remote transmission device 404 can be configured to transmit the operating parameter to one of the plurality of hydrogen generators 50 via the network, namely, the first hydrogen generator 50 (such as the leftmost hydrogen generator 50 in FIG. 8), and the first hydrogen generator 50 can perform a power-on procedure, a turn-off procedure or a setting procedure according to the operating parameter. The position monitoring device 406 can be configured to display or record the positon of each hydrogen generator 50. In practice, the positioning signal generated by the positioning device 507 of the hydrogen generator 50 can be included in the machine information $S_1$ and stored in the integrated database 402. Therefore, the position monitoring device 406 can receive the positioning signal from the integrated database 402 and display the position of the hydrogen generator 50 based on the positioning signal. In other embodiment, the machine information $S_1$ comprises the network address information of the hydrogen generator 50. The position monitoring device 406 can display or record the location of each hydrogen generator 50 based on the network address information. The data analysis device 408 can obtain the plurality of machine information from the integrated database 402, and use the machine information for analysis and judgment.

Figure 9:
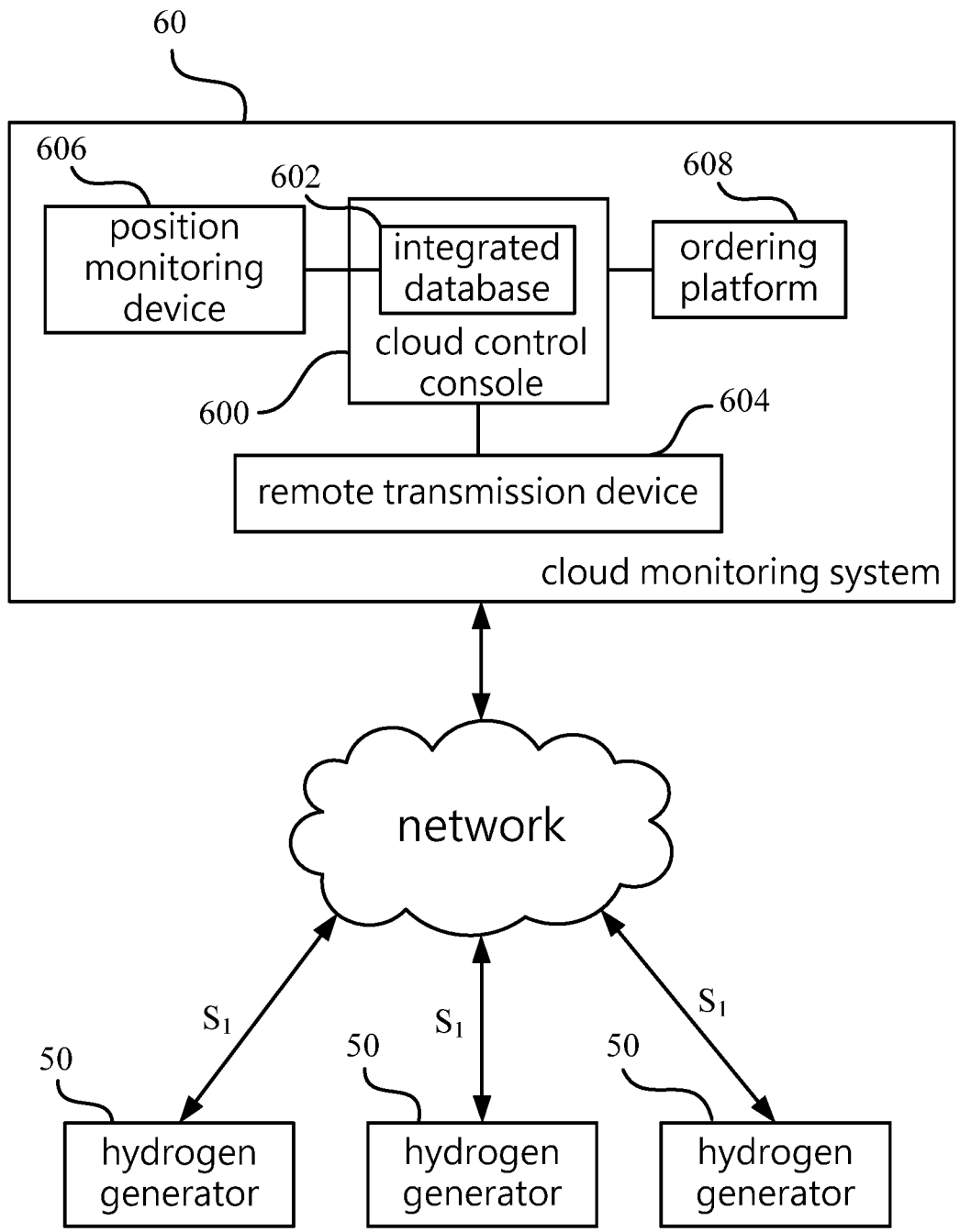
FIG. 9 is a function block diagram illustrating the cloud monitoring system and the hydrogen generator according to another embodiment of the present invention.

The cloud monitoring system in the foregoing embodiments can be configured to enable the setting of the hydrogen generator in addition to the big data analysis and the manipulation of the hydrogen generator. Please refer to FIG. 9. FIG. 9 is a function block diagram illustrating the cloud monitoring system 60 and the hydrogen generator 50 according to another embodiment of the present invention. As shown in FIG. 9, the specific embodiment is different from the foregoing embodiment in which the cloud monitoring system 60 of this specific embodiment comprises an ordering platform 608 coupled to the cloud control console 600, and the ordering platform 60 is configured for the user to input the ordering instruction. The ordering instructions are transmitted to the cloud control console 600. The order instruction input by the user comprises the predetermined position information corresponding to the predetermined position. In practice, when the user orders the hydrogen generator 50 under the platform 60, the user can fill in the position where the hydrogen generator 50 is to be installed, namely, the aforementioned predetermined position. The ordering platform 60 can send the ordering instruction with predetermined position information based on the predetermined position. The functions and the types of other components in this specific embodiment are substantially the same as those in the foregoing specific embodiments, and thus will not be described again. It should be noted that although the data analysis device is not illustrated in FIG. 9, the cloud monitoring system of the specific embodiment may further comprise a data analysis device for performing big data analysis of the machine information. In addition, the ordering platform 608 can be a personal computer, a smart phone, a tablet or any input device that can communicate with the cloud control console 600 in a wired or wireless manner. Please note that the ordering platform 608 and the cloud control console 600 can communicate with each other through the same network between the hydrogen generator 50 and the cloud monitoring system 60, or through different networks.

In this embodiment, when the cloud control console 600 receives the ordering instruction input by the ordering platform 608, the ordering instruction can be forwarded to the dealer of the hydrogen generator 50, and then the dealer distributes one of the hydrogen generators 50 (the first hydrogen generator 50) to the predetermined position specified in the ordering instruction. Please note that in practice, the ordering instruction can also order the plurality of hydrogen generators 50 at the same time and designate the delivery to multiple predetermined positions. In one embodiment, the cloud control console 600 can generate an activation parameter corresponding to the machine information $S_1$ of the first hydrogen generator 50, and the remote transmission device 604 will output the activation parameter. The activation parameter can be configured for the first hydrogen generator 50 to perform an activation procedure. In other embodiment, the first hydrogen generator 50 has a positioning device to obtain the current position of the hydrogen generator 50. The cloud control console 600 can compare the position of the first hydrogen generator 50 with the predetermined position information. When the position of the first hydrogen generator 50 matches the predetermined position corresponding to the predetermined position information, the cloud control console 600 can generate an activation parameter corresponding to the machine information $S_1$ of the first hydrogen generator 50. The remote transmission device 604 will output the activation parameter, which can be configured to let the first hydrogen generator 50 perform the activation procedure. Thereby, the steps of the activation procedure performed by the user or the installer can be saved.

In this specific embodiment, the activation parameter output by the remote transmission device 604 can be transmitted to the first hydrogen generator 50 through the same network between the first hydrogen generator 50 and the cloud monitoring system 60, then the hydrogen generator 50 directly performs the activation procedure when the hydrogen generator 50 is delivered to the predetermined position. In other embodiment, the remote transmission device 604 can output the activation parameter to the mobile device (e.g., via a text message) of the user (or the installer) or the ordering platform (e.g., as a web page message), and the user or the installer can re-enter the activation parameter to the first hydrogen generator 50 to perform the activation procedure. In other words, in this specific embodiment, the activation parameter can be considered as an activation code or an activation key of the first hydrogen generator 50.

In other embodiment, the user can receive and store the activation parameter from the remote transmission device 604 by the user's mobile device, and then remotely control the first hydrogen generator 50 to perform an activating setting procedure through the application installed in the mobile device. In other words, the user can remotely activate the first hydrogen generator 50 through the mobile device, and even the power-on procedure and turn-off procedure of the first hydrogen generator 50 can be remotely controlled through the mobile device. Similarly, as described in the previous embodiments, the mobile device can also have the function of receiving and transmitting the operating parameters to the first hydrogen generator 50; namely, the activation, power-on, turn-off, and the operation of the first hydrogen generator 50 can be completed through the mobile device. For the disabled, the convenience of use can be enhanced.

In other embodiment, after the hydrogen generator 50 is activated, the user can directly connect to the cloud monitoring system 60 through a remote device or the mobile device (such as a mobile phone, a tablet computer, or a PC). The remote device or the mobile device directly controls the first hydrogen generator 50 to directly perform the procedures of power-on, turn-off, and operation. For those elders who are unfamiliar with the operation of the hydrogen generator 50, the family members can remotely assist the elderly to perform to enhance the convenience of use. At this time, the remote device or the installable application of the mobile device can directly display the operation or the control screen of the first hydrogen generator 50 on the remote device or the mobile device for the user to perform remote control.

The ordering instruction is an instruction generated by the user ordering the hydrogen generator 50 through the ordering platform 608. Therefore, the ordering instruction may comprise information required for ordering such as user information and the predetermined position of the delivery. In addition, the ordering instructions may comprise other information to make the cloud monitoring system of the present invention more industrially beneficial.

In one specific embodiment, the integrated database 602 can further store a list of recommenders, and when the user inputs the order instruction through the ordering platform 608, the order instruction comprises the recommender information. In practice, the user can input the recommender information by himself/herself to make the ordering instruction comprise the recommender information, or different ordering platforms 608 have different built-in recommender information, and the user does not need to input the information as the ordering instruction already comprises the recommender information. When the cloud control console 600 receives the ordering instruction, the recommender information in the ordering instruction may be compared to the list of the recommenders in the integrated database 602 to generate the recommender profit information, and the recommender profit information may be stored in the integration database 602. Therefore, in practice, the recommender can allocate a partial profit when the hydrogen generator 50 is sold, so that the recommender is more motivated to recommend the hydrogen generator of the present invention, which can promote its commercial effect.

In other embodiment, the integrated database 602 can further store a dealer list, and when the user inputs the ordering instruction through the ordering platform 608, the ordering instruction comprises the dealer information. Similarly, the user can input the recommender information by himself/herself to make the ordering instruction comprise the dealer information, or different ordering platforms 608 have different built-in dealer information, and the user does not need to input the information as the order instruction already comprises the recommender information. For example, the user can go directly to a physical store of the dealer, and order a hydrogen generator through the ordering platform set in the store. The ordering platform in the store can directly set the order information comprising the dealer information, and the user does not need to key-in information again. When the cloud control console 600 receives the ordering instruction, the dealer information in the ordering instruction can be compared with the dealer list in the integrated database 602 to generate a dealer profit information and a repair information, and store them in the integrated database. Therefore, in practice, the dealer can allocate a part of the profit when the hydrogen generator 50 is sold and can be responsible for the subsequent machine maintenance, which can further promote its commercial effect.

In addition, according to another embodiment, the cloud monitoring system of the present invention can be configured to monitor the plurality of hydrogen generators. The cloud monitoring system of this specific embodiment may comprise the integrated database, the ordering platform, the cloud control console, the remote transmission device, and the position monitoring device. Wherein the cloud control console may be coupled to the ordering platform, the remote transmission device is coupled to the cloud control console, and the position monitoring device is coupled to the integrated database. The integrated database may comprise or store a profit person list, and the profit person list may be the recommender list, the dealer list or both.

In this embodiment, the user can input the ordering instruction through the ordering platform to purchase the first hydrogen generator (i.e., one of the plurality of hydrogen generators monitored by the cloud monitoring system). The ordering instruction can comprise the predetermined position information or the specific profit person information. The predetermined position information is the information of the position where the user wishes to distribute the first hydrogen generator, and the specific profit person information is the recommender information, the dealer information or both. The cloud control console can receive the ordering information input by the user from the ordering platform, and generate the activation parameter of the first hydrogen generator according to the order information. The remote transmission device can receive and output the activation parameter from the cloud control console. The first hydrogen generator can perform the setting procedure according to the activation parameter, so that the user can start using the first hydrogen generator.

In this specific embodiment, when the first hydrogen generator ordered by the user reaches the position corresponding to the predetermined position information, that is, the position specified by the user, the activation setting procedure is started. In detail, the cloud control console can obtain the current position of the first hydrogen generator by receiving the positioning signal of the first hydrogen generator, and can display the current position by the position monitoring device, and then compare the current position of the first hydrogen generation with the predetermined position information. When the current position of the first hydrogen generator matches the predetermined position corresponding to the predetermined position information, the cloud control console controls the remote transmission device to output the activation parameter to let the first hydrogen generator start to perform the activation setting procedure. The remote transmission device can output the activation parameters in different ways. For example, the remote transmission device can transmit the activation parameter to a mobile device in a short message manner, or transmit the activation parameter to the ordering platform and present it on the webpage of the ordering platform. Therefore, the user or the installer can know the activation parameter, and then input the activation parameter to let the first hydrogen generator perform the activation setting procedure. In practice, the remote transmission device may also directly transmit the activation parameter to the first hydrogen generator to perform the activation setting procedure when the first hydrogen generator is in the predetermined position.

As mentioned above, the integrated database of this specific embodiment can store the profit person list, and the order instructions input by the user through the ordering platform can also comprise the specific profit person information. Therefore, after receiving the ordering instruction, the cloud control console not only achieves the delivery and activation of the first hydrogen generator, but also achieves different profit modes.

In one specific embodiment, the user can input the recommender information on the ordering platform. For example, the information about the doctors who recommend such hydrogen generators is used as the information for specific profit person information. When the cloud control console receives the ordering instruction, the cloud control console compares the recommender information with the recommender list in the integrated database. If the comparison result is that the recommender corresponding to the recommender information is listed in the recommender list, the cloud control console may generate the profit person information correspondingly according to the recommender information. In practice, according to the recommender profit information, a part of the profit can be given to the recommender who sells the first hydrogen generator, so that the recommender has an incentive to sell the hydrogen generator to achieve better commercial effects.

In other embodiment, the user can enter the dealer information on the ordering platform. For example, a store or an agent that sells the hydrogen generator as a specific profit person information. When the cloud control console receives the ordering instruction, the cloud control console will compare the dealer information with the dealer list in the integrated database. If the result of the comparison is that the dealer corresponding to the dealer information is listed in the dealer list, the cloud control console can generate the dealer profit information according to the dealer information. In practice, according to the dealer profit information, the profit distribution obtained by selling the first hydrogen generator can be given to the dealer. In addition, the dealer information corresponding to the first hydrogen generator can also be stored in the integrated database. If the first hydrogen generator fails in the future, the dealer can directly repair to obtain the repair profit. Therefore, dealers have an incentive to promote hydrogen generators to achieve better commercial results.

In other embodiment, the user can simultaneously input the dealer information and the recommender information on the ordering platform. For example, the above-mentioned information of a store or an agent who sells a hydrogen generator or a doctor who recommends such hydrogen generators is used as the specific profit person information. When the cloud control console receives the ordering instruction, the cloud control console will compare the dealer information with the dealer list in the database and compare the recommender information with the recommender list. Similarly, if the comparison result is that the dealer corresponding to the dealer information is listed in the dealer list and the recommender corresponding to the recommender information is listed in the recommender list, the cloud control console can generate the dealer profit information and the recommender profit information according to the dealer information and the recommender information. In practice, according to the dealer profit information and the recommender profit information, a part of the profit distribution obtained by selling the first hydrogen generator can be given to the dealer and the other part is given to the recommender. Therefore, dealers and recommenders have incentives to promote hydrogen generators to achieve better commercial results.

In summary, the cloud monitoring system of the present invention can achieve a plurality of different profit sharing modes, so that recommenders, dealers, and the cloud monitoring system can cooperate among themselves, which improves the sales volume of the hydrogen generators or other similar electronic products and provides the perfect after-sales service.

Compared with the prior art, the cloud monitoring system of the hydrogen generator of the present invention uses the machine information of the hydrogen generator and the physiological information of the user to perform big data analysis. Through the return and analysis of data, the data will be used most efficiently in industries. Compared with other hydrogen generators on the market, the cloud monitoring system of the hydrogen generator of the present invention not only increases the safety of the hydrogen generator, but also provides a personalized service project and has academic value.

With the examples and explanations mentioned above, the features and spirits of the invention are hopefully well described. More importantly, the present invention is not limited to the embodiment described herein. Those skilled in the art will readily observe that numerous modifications and alterations of the device may be made while retaining the teachings of the invention. Accordingly, the above disclosure should be construed as limited only by the metes and bounds of the appended claims.

What is claimed is:

1. A cloud monitoring system for monitoring a plurality of hydrogen generators, comprising:
   a cloud control console configured to receive a plurality of machine information from the plurality of hydrogen generators and to receive a plurality of physiological information of user from a plurality of physiological information input device, wherein the physiological information comprises a blood oxygen concentration value, a heartbeat index, a respiratory function value or a blood pressure value;
   an integrated database configured to store the plurality of machine information of the plurality of hydrogen generators and the plurality of physiological information;
   a remote transmission device coupled to the cloud control console and configured to transmit an operating parameter to a first hydrogen generator of the plurality of hydrogen generators, whereby the first hydrogen generator performs a turn-on procedure, a turn-off procedure or a setting procedure according to the operating parameter; and
   a data analysis device coupled to the integrated database and configured to perform big data analysis with the plurality of physiological information and/or the plurality of machine information to generate the operating parameter; the data analysis device being configured to perform big data analysis with the plurality of physiological information for medical research.

2. The cloud monitoring system of the claim 1, wherein the remote transmission device transmits the operating parameter to the first hydrogen generator when the data analysis device ascertains that a set of machine information corresponding to the first hydrogen generator comprise an abnormal information, whereby the first hydrogen generator performs the turn-off procedure or the setting procedure according to the operating parameter.

3. The cloud monitoring system of the claim 1, wherein the operating parameter is transmitted to the first hydrogen generator by a mobile device via the remote transmission device, whereby the first hydrogen generator performs the turn-on procedure, a turn-off procedure or the setting procedure according to the operating parameter.

4. The cloud monitoring system of the claim 1, wherein the integrated database further stores a plurality of authentication information or a plurality of physiological characteristic information of a plurality of users of the plurality of the hydrogen generators, and stores a plurality of physiological information of the plurality of users, wherein the data analysis device analyzes the plurality of physiological information of the plurality of users and generates the operating parameter.

5. The cloud monitoring system of the claim 1, wherein the integrated database further stores a plurality of de-identification physiological information of a plurality of users of the plurality of the hydrogen generators, wherein the data analysis device analyzes the plurality of de-identification physiological information of the plurality of users and generates the operating parameter.

6. The cloud monitoring system of the claim 1, wherein the plurality of machine information stored in the integrated database are de-identified machine information.

7. The cloud monitoring system of the claim 1, further comprising a position monitoring device coupled to the integrated database to display a plurality of positions of the plurality of hydrogen generators on a map.

8. A cloud monitoring system for monitoring a plurality of hydrogen generators, comprising:
    an integrated database configured to store the plurality of machine information of the plurality of hydrogen generators and a plurality of physiological information of user from a plurality of physiological information input device, wherein the physiological information comprises a blood oxygen concentration value, a heartbeat index, a respiratory function value or a blood pressure value, and the integrated database further including a profit person list, wherein the plurality of physiological information of user and/or the plurality of machine information are used for big data analysis to generate operating parameters for the hydrogen generators, and the plurality of physiological information of user are used for big data analysis for medical research;
    an ordering platform configured for a user to input an order instruction of a first hydrogen generator, and the order instruction including a predetermined position information or a specific profit person information;
    a cloud control console coupled the ordering platform, and the cloud control console configured to receive the order instruction and generate an activation parameter of the first hydrogen generator according to the order instruction;
    a remote transmission device coupled to the cloud control console and configured to receive the activation parameter from the cloud control console; and
    a position monitoring device coupled to the integrated database to display or record the positions of the plurality of hydrogen generators;
    wherein the remote transmission device outputs the activation parameter, whereby the first hydrogen generator performs an activation setting procedure according to the activation parameter.

9. The cloud monitoring system of the claim 8, wherein the cloud control console is configured to compare the position of the first hydrogen generator with the predetermined position information; when the position of the first hydrogen generator matches a predetermined position corresponding to the predetermined position information, the cloud control console controls the remote transmission device to output the activation parameter corresponding to the first hydrogen generator, whereby the first hydrogen generator performs the activation setting procedure according to the activation parameter.

10. The cloud monitoring system of the claim 8, wherein the cloud control console controls the remote transmission device to output the activation parameter to a mobile device or the ordering platform.

11. The cloud monitoring system of the claim 8, wherein the cloud monitoring system is configured for a mobile device to be coupled to, whereby the mobile device remotely controls the first hydrogen generator to perform an operating procedure.

12. The cloud monitoring system of the claim 8, wherein the profit person list is a recommender list and the specific profit person information is a recommender information, the cloud control console compares the recommender information with the recommender list of the integrated database after receiving the order instruction, and generates a recommender profit information according to the recommender information.

13. The cloud monitoring system of the claim 8, wherein the profit person list is a dealer list and the specific profit person information is a dealer information, the cloud compares the dealer information with the dealer list of the integrated database after receiving the order instruction, and generates a dealer profit information according to the dealer information.

14. The cloud monitoring system of the claim 8, wherein the profit person list comprises a dealer list and a recommender list, and the specific profit person information comprises a dealer information and a recommender information, the cloud control console compares the recommender information and the dealer information with the recommender list and the dealer list of the integrated database after receiving the order instruction, and generates a recommender profit information and a dealer profit information according to the recommender information and the dealer information.

\* \* \* \* \*